US005492830A

United States Patent [19]
Kalwass et al.

[11] Patent Number: 5,492,830
[45] Date of Patent: Feb. 20, 1996

[54] ENZYMATIC RESOLUTION OF α-TERTIARY CARBOXYLIC ACID ESTERS

[75] Inventors: Helmut Kalwass, Belmont; Christopher Yee, Needham; Todd Blythe, Malden; Spencer Shames, Concord; Elizabeth Rogers, Cambridge, all of Mass.

[73] Assignee: Genzyme Corporation, Cambridge, Mass.

[21] Appl. No.: 83,943

[22] Filed: Jun. 25, 1993

Related U.S. Application Data

[63] Continuation-in-part of Ser. No. 870,061, Apr. 17, 1992, abandoned, which is a continuation-in-part of Ser. No. 697,152, May 8, 1991, Pat. No. 5,202,260.

[51] Int. Cl.$^6$ ............... C12N 9/48; C12P 7/62; C12P 41/00
[52] U.S. Cl. ............ 435/280; 435/41; 435/135; 435/212
[58] Field of Search ............ 435/280

[56] References Cited

U.S. PATENT DOCUMENTS

| | | | |
|---|---|---|---|
| 3,405,159 | 10/1968 | Krieger et al. | 558/354 |
| 3,830,827 | 8/1974 | Karady et al. | 560/34 |
| 3,895,052 | 7/1975 | Karady et al. | 560/34 |
| 4,262,092 | 4/1982 | Bauer | 435/280 |
| 5,202,260 | 4/1993 | Yee et al. | 435/280 |

OTHER PUBLICATIONS

Breddam, K.; Carlsberg Res. Comm. 51: 83–128 (1986).
Christen, M. et al.; J. Chem. Soc., Chem. Commun., No. 4, pp. 264–266, 1988.
Kato, Y. et al.; Tetrahedron Letters 28: 1303–1306 (1987).
Chenault, H. K. et al (1989) "Kinetic Resolution of Unnatural and Rarely Occurring Amino Acids: Enantioselective Hydrolysis of N–Acyl Amino Acids Catalyzed by Acylase I" *J. Am. Chem Soc.* 111:6354–6364.
Fluka Chemika/Biochemika 1988–1989 Catalog 16. Fluka Chemical Corp., Ronkonkoma, New York, p. 797 (1988).
Sugai, T. et al (1990) "Enzymatic Preparation of Enantiomerically Enriched Tertiary A–Benzyloxy Acid Esters. Application to the Synthesis of (S)–(–) Frontalinl" *J. Org. Chem.*, 55:4643–4647.

*Primary Examiner*—Robert A. Wax
*Assistant Examiner*—Eric Grimes
*Attorney, Agent, or Firm*—William G. Gosz

[57] ABSTRACT

A method for the resolution of α-tertiary carboxylic acid esters by partial hydrolysis is disclosed. The partial hydrolysis is carried out by contacting the esters with an aqueous solution in the presence of a serine carboxypeptidase, and the hydrolysis product is separated from unreacted starting material to obtain the hydrolysis product or the unreacted starting material in enantiomerically enriched form. A novel ester hydrolase which is particularly useful in this method, and a nucleotide sequence encoding this enzyme, are also described.

12 Claims, No Drawings

ENZYMATIC RESOLUTION OF α-TERTIARY CARBOXYLIC ACID ESTERS

CROSS REFERENCE TO RELATED APPLICATIONS

This application is a continuation-in-part of U.S. application Ser. No. 870,061, filed Apr. 17, 1992, now abandoned, which is a continuation-in-part of U.S. application Ser. No. 697,152, filed May 8, 1991, now U.S. Pat. No. 5,202,260.

BACKGROUND OF THE INVENTION

The present invention relates to a method for preparing optically active acids and their corresponding esters by partial enzymatic hydrolysis of α-tertiary carboxylic acid esters using enzymes classified as serine carboxypeptidases or structurally and catalytically homologous enzymes. Such enzymes are generally classified by the Enzyme Commission in class EC 3.4.16.1. The method of this invention is useful in preparing compounds which have utility as starting materials and intermediates for the synthesis of pharmaceutical, agricultural and veterinary products.

Review articles on enzymatic synthesis, such as D. H. G. Crout and M. Christen, *Modern Synthetic Methods*, vol. 5 (1989, Springer-Verlag and J. B. Jones, *Tetrahedron*, 42, 3351 (1986), describe many examples of the enzymatic resolution of esters in which the α-carbon possesses one hydrogen atom. However, relatively little information has been reported for the enzymatic resolution of carboxylic acids or esters in which the α-carbon is fully substituted with moieties other than hydrogen.

Chenault et al., *J. Am. Chem. Soc.*, 111, 6354 (1989), describe the resolution of eight 2-amino-2-methyl carboxylic acids by partial hydrolysis of the amide moieties of racemic 2-N-acylamino- 2-methyl carboxylic acids with acylase I from porcine kidney and from the fungus Aspergillus species. The enzymes display (S)-stereoselectivity, and three of the L-2-methylamino acids were prepared in greater than 90% enantiomeric excess. Results of the resolution of the N-acylmethyldopa derivative were not disclosed. The reported enzymatic resolutions require as much as twice the weight of enzyme to substrate and about eleven days to achieve 50% hydrolysis, and are therefore limited in their applications and in their usefulness in commercial processes.

Sugai et al., *J. Org. Chem.* 55, 4643 (1990) describe the resolution of the racemic methyl ester of 2-benzyloxy-2-methyl-4 -pentenoic acid (an α-oxygen substituted ester) to yield the optically pure (S)-acid which was subsequently used in the synthesis of (1S,5R)-(–)-frontalin, a constituent of the aggregation pheromone of the female southern pine bark beetle. The enantiomerically pure {S)-acid was obtained by enzymatically hydrolysing the racemic ester with *Candida cylindracea* lipase, isolating and then re-esterifying the enantiomerically enriched (S)-acid, and recontacting the optically enriched (S)-ester with *Candida cylindracea* lipase for additional hydrolysis. This sequence for preparing (S)-2-benzyloxy- 2-methyl-4-pentenoic acid that requires two enzymatic resolution steps results in longer overall reaction times and lower chemical yields than a process which employs only one enzymatic resolution step. Enzymatic resolution of α-tertiary 2-hydrazino-2-methyl carboxylic acid esters has not previously been reported in the literature. Such compounds are useful in the production of amino acid decarboxylase inhibitors, and in particular carbidopa, which is used in the treatment of Parkinson's disease. The current methods of production of compounds such as carbidopa employ chemical resolution of 2-hydrazino (U.S. Pat. No. 3,895,052) or 2-amino (U.S. Pat. No. 3,405,159) precursors. Such methods require expensive chiral auxiliaries or costly and complicated equipment. See also U.S. Pat. No. 3,830,827, which describes a chemical method for preparing carbidopa.

SUMMARY OF THE INVENTION

We have discovered that serine carboxypeptidases as defined herein are effective in resolving a variety of s-tertiary carboxylic acid esters of general formula

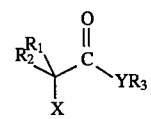

wherein $R_1$ and $R_2$ independently represent alkyl, substituted alkyl, alkenyl, substituted alkenyl, alkynyl, substituted alkynyl, aryl, wherein $R_1$ and $R_2$ independently represent alkyl, substituted alkyl, alkenyl, substituted alkenyl, alkynyl, substituted alkynyl, aryl, substituted aryl, arylalkyl or substituted arylalkyl, or $R_1$ and $R_2$ together are linked to form a cyclic structure incorporating the asymmetric α-carbon atom; $R_3$ represents an alkyl moiety having from 1 to 8 carbon atoms, substituted alkyl, alkenyl, substituted alkenyl, alkynyl, substituted alkynyl, aryl, substituted aryl, arylalkyl or substituted arylalkyl; X represents alkyl, substituted alkyl, halogen, amino, alkylamino, arylalkylamino, arylamino, acylamino, hydrazino, alkylhydrazino, arylalkylhydrazino, arylhydrazino, acylhydrazino, hydroxyl, alkoxy, arylalkoxy, aryloxy, mercapto, alkylthio, arylalkylthio or arylthio; and Y represents oxygen or sulfur; provided that $R_1$, $R_2$ and X are different from each other. Serine carboxypeptidases have now been found to hydrolyze with moderate to high selectivity one isomer of a mixture of enantiomers of α-tertiary carboxylic acid esters. The resolution of these esters can be accomplished by the partial hydrolysis of a solution or suspension of the ester in a predominantly aqueous mixture in the presence of the serine carboxypeptidase, and separating the product acid from the starting ester. Separation is advantageously accomplished by methods well known to skilled practitioners of this art, such as by extraction, chromatography and selective precipitation. The selectivity of the present method permits the hydrolysis of predominantly one enantiomer, and preferably only one enantiomer.

In one aspect, the method of this invention can be applied to the enzymatic resolution of 2-hydrazino and 2-β-N-acylhydrazino) esters, and in particular, alkyl 2-hydrazino-2-methyl-3-(4-hydroxy- 3-methoxyphenyl)propionates and alkyl 2-(β-N-acylhydrazino)-2-methyl- 3-(4-hydroxy-3-methoxyphenyl)propionates, the ester precursors of carbidopa. For the optical resolution of these esters, the method is carried out in aqueous medium, and the enzymatic reaction stops after the (S)-ester is hydrolyzed. The (S)-acid and (R)-ester can be conveniently separated, and the enantiomeric excess of each determined.

In another aspect, the method of this invention can also be applied to the resolution of 2-amino-2-methyl carboxylic acid esters, such as alkyl 2-amino-2-methyl-3-(3,4-dihydroxyphenyl)-propionates, which are precursors to the antihypertensive agent methyldopa. Enzymatic hydrolysis of the ester function of methyldopa esters affords (S)-methyldopa and the corresponding (R)-alkyl esters.

Other compounds that can be enzymatically resolved using the method of this invention include α-tertiary 2-hydroxy carboxylic esters and s-tertiary 2-halomethyl carboxylic esters, such as racemic ethyl 2-hydroxy-2-methyl-3-(3, 4-dimethoxyphenyl)-propionate and α-difluoromethylphenylalanine methyl ester, respectively.

A further aspect of this invention includes a novel enzyme derived from *Candida lipolytica* that is homologous to known serine carboxypeptidases and has an N-terminal sequence as described herein, as well as nucleotide sequences encoding said enzyme. The use of this novel enzyme is first described in U.S. Pat. No. 5,202,260, the disclosure of which is incorporated by reference herein.

The method of this invention is convenient, requires no costly or complicated equipment, and can be readily adopted for large-scale production of enantiomerically enriched α-tertiary carboxylic acids and their corresponding esters. The use of a serine carboxypeptidase or the hydroiasc isolated from *Candida lipolytica* also has the advantages of greater hydrolyric activity and enantioselectivity than *Candida cylindracea* lipase with respect to the synthesis of 2-hydroxy-2-methyl or 2-alkoxy-2-methyl carboxylic acids, resulting in simplified and higher-yielding processes.

The compounds of this invention are useful as intermediates in the synthesis of pharmaceutical, agricultural and veterinary products.

DESCRIPTION OF THE PREFERRED EMBODIMENTS

The chiral acids and their corresponding esters of this invention can be generally obtained as follows. A racemic carboxylic acid ester of the general formula

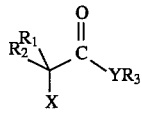

I wherein $R_1$ and $R_2$ independently represent alkyl, substituted alkyl, alkenyl, substituted alkenyl, alkynyl, substituted alkynyl, aryl, substituted aryl, arylalkyl or substituted arylalkyl, or $R_1$ and $R_2$ together are linked to form a cyclic structure incorporating the asymmetric α-carbon atom; $R_3$ represents an alkyl moiety having from 1 to 8 carbon atoms, substituted alkyl, alkenyl, substituted alkenyl, alkynyl, substituted alkynyl, aryl, substituted aryl, arylalkyl or substituted arylalkyl; X represents alkyl, substituted alkyl, halogen, amino, alkylamino, arylalkylamino, arylamino, acylamino, hydrazino, alkylhydrazino, arylalkylhydrazino, arylhydrazino, acylhydrazino, hydroxyl, alkoxy, arylalkoxy, aryloxy, mercapto, alkylthio, arylalkylthio or arylthio; and Y represents oxygen or sulfur; provided that $R_1$, $R_2$ and X are different from each other, is dissolved or suspended in water or an aqueous buffer so that the final concentration of the substrate ranges from 0.001 to 6.0 moles per liter of reaction volume. The molarity of the buffer may range from 0.001 to 0.5 M, but to facilitate the isolation of the product acid, water or 0.01 to 0.05 M buffer is preferred. The concentration of the buffer may be increased or decreased for convenience in conducting the enzymatic hydrolysis or product isolation. The pH of the resulting solution or suspension is adjusted to between 4 and 8.5. The aqueous medium can also include up to about 75%, but preferably less than 15%, by volume of a miscible organic solvent, including but not limited to methanol, ethanol, 1-propanol, 2-propanol, acetone, 2-butanone, acetonitrile, dimethylformamide or dimethylsulfoxide. The use of a water miscible organic solvent may serve to improve the solubility of certain substrates.

A serine carboxypeptidase enzyme is added to the substrate mixture to initiate the reaction and the resulting mixture is agitated. The optimum amount of enzyme used varies with the protein content of the enzyme preparation, the structure of the target substrate and the reaction temperature, with a range of from 1 to 200 mg of protein per gram of substrate being preferred. It should be noted that higher or lower protein to substrate ratios are also useful in carrying out the desired resolutions, but at the expense of greater enzyme cost or longer reaction times, respectively. The optimum reaction temperature at which the hydrolysis is conducted may vary, and can range from 0° C. to 55° C., but 15° C. to 37° C. is preferred. The atmosphere above the reaction may be air, or an inert gas, such as nitrogen. If the reaction proceeds for more than two days or at elevated temperatures, an inert atmosphere is preferred.

The enzyme of this invention is a hydrolase which means that it is capable of hydrolysing selected substrates, in this case the substrates identified by general formula I. These enzymes are also known to catalyze the sequential hydrolysis of single amino acid residues from the C-termini of peptides, and are characterized by maximum peptidoiytic activity in acid pH range and sensitivity to inhibition by organic fluorophosphates. Such enzymes are referred to herein as "serine carboxypeptidases" in accordance with accepted nomenclature, and are further identified by E.C. 3.4.16.1. Particular enzymes which are included in this category include the *Candida lipolytica* hydrolase described in U.S. Pat. No. 5,202,260, and the Y, W, and P serine carboxypeptidases which are more fully described herein.

The serine carboxypeptidases used in this invention, i.e. Y, W and P are commercially available and derived from *Saccharomyces cerevisiae*, wheat (*Triticum aestivum*) and *Penicillium janthinellum*, respectively. The use of the ester hydrolase derived from *Candida lipolytica*, also known as *Yarrowia lipolytica*, is also described. Crude preparations containing this ester hydrolase are commercially available and sold as *Candida lipolytica* lipase. A particularly preferred source of the *Candida lipolytica* ester hydrolase for purposes of this invention is the commercial enzyme available from Fluka Chemie AG, which is sold under the name "Lipase from *Candida lipolytica*". The commercial enzyme is actually believed to be a mixture of at least six discrete protein species as determined by SDS-polyacrylamide gel electrophoresis (SDS-PAGE), various salts and buffer components and the like, as well as water insoluble material.

The crude ester hydrolase of *Candida lipolytica* that is obtained from commercial suppliers may be used in the resolution of the present substrates without modification. Equally effective in resolving these substrates are either partially purified or homogeneous ester hydrolase. Serine carboxypeptidases Y, W and P are commercially available as purified enzymes. The ester hydrolase from *Candida lipolytica* may be obtained as commercially available crude lipase or from the fermentation broth of an appropriate *Candida lipolytica* strain. Partial purification of the ester hydrolase may be accomplished by chromatography on a variety of resins including, but not limited to, ion exchange, hydrophobic, dye-ligand and hydroxylapatite.

A two-step process may be employed to purify the ester hydrolase of *Candida lipolytica* to greater than 90% homogeneity from commercially available lipase preparations. Following an extraction of the crude lipase into a suitable buffer and removal of insoluble components, a protein fraction containing the ester hydrolase activity may be precipitated with polyethylene glycol. The extraction may be carried out using any standard biological buffer known to those skilled in the art, such as Hepes, phosphate or Tris, in the pH range of 6.0–9.0, with the preferred buffer solution being 10 mM phosphate, pH 6.5, containing 1.0 mM EDTA. Insolubles may be removed from the extraction mixture by methods standard in the art including either filtration of centrifugation.

Purification of the ester hydrolase from the isolated protein fraction may be accomplished by column chromatography using a variety of resins with the preferred resin being Amicon Blue B Matrex™ (Amicon Corp., Danvers, Mass.). Chromatography on the Blue B Matrex™ resin may be accomplished at a pH between 6.0 and 7.0, with the preferred purification buffer being I0 mM phosphate, pH 6.5, containing 1.0 mM EDTA.

After washing the resin with buffer to remove contaminating proteins, the ester hydrolase may be etuted from the dye resin with a high ionic strength buffer. The preferred buffer for elution of the ester hydrolase is 10 mM sodium phosphate, pH 6.5, containing 1.0 mM EDTA and 1.2 M KCl.

The ester hydrolase may also be purified to >90% homogeneity from the fermentation broth of an appropriate *Candida lipolytica* strain. Following the removal of cells from the fermentation broth, a protein fraction containing the ester hydrolase may be isolated by precipitation with polyethylene glycol or by chromatography on a suitable resin known to those skilled in the art. One chromatographic method of isolation is hydrophobic chromatography on phenyl sepharose resin (Pharmacia, Piscataway, N.J.). The ionic strength of the fermentation broth may be increased with a salt such as 1.8 M ammonium sulfate and applied directly to a phenyl sepharose column equilibrated in a high ionic strength buffer such as 50 mM Hepes, pH 7.5, containing 1.0 mM EDTA and 1.8 M ammonium sulfate.

After washing the hydrophobic resin with high ionic strength buffer, a protein fraction containing the ester hydrolase may be eluted with a low ionic strength buffer such as 50 mM Hepes, pH 7.5, containing 1.0 mM EDTA. The eluant may be adjusted to 30% polyethylene glycol to precipitate the proteins and remove residual salts or dialyzed prior to chromatography on Blue B Matrex™ dye resin.

Ester hydrolase purified from crude commercial lipase preparations or from the fermentation broth of *Candida lipolytica* strain MARL-Y1094 migrates as a diffuse band between 60,000 and 120,000 Daltons on a Comassie blue-stained 8% SDS-polyacryalamide gel. Ester hydrolase that has been purified according to the general procedure described above can be treated with either N-Glycanase® enzyme (Genzyme Corp., Cambridge, Mass.) or endo-β-N-acetylglucosaminidase H (Endo H) enzyme to remove N-linked carbohydrates prior to analysis by SDS-polyacrylamide gel electrophoresis. The treated protein migrates as a single sharp band with a mobility corresponding to a molecule weight of ≈55,000 Daltons.

These data suggest that in similar fashion to other known serine carboxypeptidases, the *Candida lipolytica* ester hydrolase is a glycoprotein. N-Terminal sequence analysis of *Candida lipolytica* ester hydrolase purified from commercial lipase preparations or from the fermentation broth of *Candida lipolytica* strain NRRL-Y1094 revealed the following sequence:

| SER | VAL | PRO | GLY | ASP | LEU | GLY | LEU | ASP | ASP |
|-----|-----|-----|-----|-----|-----|-----|-----|-----|-----|
| 1   |     |     |     | 5   |     |     |     |     | 10  |
| VAL | GLN | GLN | TYR | THR | GLY | TYR | LEU | THR | ALA |
|     |     |     |     | 15  |     |     |     |     | 20  |

This N-terminal sequence defines a novel ester hydrolase as more particularly described herein.

To examine the homology between the *Candida lipolytica* ester hydrolase and serine carboxypeptidases (E.C. 3.4.16.1), various structural and kinemic characterization studies were carried out. First, the primary sequence of several internal peptides was determined. Peptide fragments were generated by treatment with endoproteinase Lys-C, endoproteinase Glu-C, trypsin and cyanogen bromide via standard methods. Following purification by reverse phase HPLC, the sequences of individual selected peptides were determined by Edman degradation using standard protocols on automated sequencers. The resulting sequences of internal peptides showed strong homology to known member's of the group of serine carboxypeptidases (E.C. 3.4.16.1

To determine if the *Candida lipolytica* hydrolase had peptidolytic and amidolytic activities, the activity of the *Candida lipolytica* enzyme was examined using the dipeptide substrate N-Cbz-Phe-Ala and the chromogenic substrate benzoyl-L-tyrosine p-nitroanilide, respectively. These substrates have been used routinely for determining carboxypeptidase activity (Johansen et al., *Carlsberg Res. Commun.*, vol. 41, p. 4,(1976) and Hayashi, R., *Methods in Enzymology*, vol. 45, p. 568, (1976) respectively). Using the standard reaction conditions, the *Candida lipolytica* ester hydrolase showed hydrolyric activity with both of these substrates.

To determine if the active site of *Candida lipolytica* ester hydrolase contained an activated serine residue as in known serine carboxypeptidases, the sensitivity of the enzyme towards inactivation by the organic fluorophosphate diisopropyl fluorophosphate (DFP) was examined. Using thiopropyl D,L-N-acetyl-α-methylphenylalanate as the assay substrate, the enzyme was found to be rapidly inhibited by DFP at concentrations of 0.1–1 mM or higher, that is coramonly observed with serine proteases (Dawson et al., Data for Biochemical Research, 1986, 3rd edition, p. 321, Oxford Science Publications). The *Candida lipolytica* enzyme was also sensitive to inhibition with phenylmethylsulfonyl fluoride (PMSF), another inhibitor that is specific for enzymes with catalytically active serine residues. Incubation of the *Candida lipolytica* ester hydrolase with 1 mM PMSF resulted in complete inactivation of esterase activity as evaluated with thiopropyl D,L-N-acetyl-α-methylphenylalanate as the substrate.

Taken together, the above structural and kinetic data suggest the novel *Candida lipolytica* ester hydrolase of this invention to be closely related to the known members of the group of serine carboxypeptidases identified by E.C. 3.4.16.1. Accordingly, this enzyme is also referred to herein as a serine carboxypeptidase.

It has also been found that the serine carboxypeptidases of this invention can be immobilized on various solid supports without loss of stereospecificity or change in stereoselectivity. The solid supports can either be inert adsorbents to which the enzyme is not covalently bonded, but instead is adsorbed by any number of phenomena including, but not limited to, interactions of hydrophobic or hydrophilic portions of a protein with like regions of the inert absorbent, by hydrogen bonding, by salt bridge formation, or by electrostatic interactions. Inert absorbent materials include, but are not limited to, synthetic polymers (e.g. polystyrene, poly(vinylalcohol), polyethylene and polyamides), mineralaceous compounds (e.g. diatomaceous earth and Fuller's earth), or naturally occurring polymers (e.g. cellulose). Specific examples of such materials include Celite 545 diatomaceous earth, Aberlite XAD-8 polymeric resin beads and polyethylene glycol 8000. The enzyme may also be immobilized on supports to which the enzyme is covalently bonded (e.g. oxirane-acrylic beads and glutaraldehyde activated supports). Specific examples include Eupergit C oxirane-acrylic beads and glutaraldehyde activated Celite 545. Other possible immobilizing systems are well known and are readily available to those skilled in the art of enzyme immobilization, including the immobilization of serine carboxypeptidase Y (H. Y. Hsiao and G. P. Royer, *Arch. Biochem. Biophys.*, 198, 379 (1979)). These immobilized enzyme preparations offer more predictable results, simplify reaction processes and product isolation, and reduce the cost of the enzyme.

The initial pH of the reaction mixture can be maintained by constant addition of an inorganic base, such as sodium hydroxide, or by the use of a suitable buffer. The extent of hydrolysis is monitored by the amount of base added or by periodic withdrawal of aliquots of the reaction mixture and measuring the relative amounts of starting material and product by high pressure liquid chromatography. For the purpose of making the optically active acid, the reaction may be terminated after 5% to 50% hydrolysis has occurred, but to maximize chemical yield, 40% to 50% hydrolysis is preferred.

The product is separated from the unreacted ester by adjusting the pH of the reaction mixture to 7.5–8.0 and extracting the ester with an organic solvent such as methylene chloride, ethyl acetate, diethyl ether, or any other volatile solvent in which the substrate is stable and soluble, and which is also immiscible in the aqueous phase. Concentration of the organic extracts affords the unreacted ester, while concentration of the aqueous phase yields the acid which can be freed of buffer salts by selective precipitation or chromatography, or other methods known to those skilled in the art.

Alternatively, the reaction mixture may be acidified, e.g. to pH 3, and both the ester and acid extracted into organic solvents such as methylene chloride, ethyl acetate, diethyl ether, or any volatile solvent in which the substrate is stable, soluble and which is immiscible with the aqueous phase. Concentration of the organic extract yields a mixture of the ester and acid, and these may be separated by selective precipitation or chromatography, or by other methods known to those skilled in the art. Methods for determining the enantiomeric excess of the esters and the acids depend on the nature of the substituent X, and are illustrated by the examples that are described hereinafter.

The chiral esters are prepared by a method similar to that described for the preparation of the chiral acids. The difference is that the hydrolysis is allowed to proceed to 50% to 95%, but in the interest of maximizing the chemical yield, 50% to 60% hydrolysis is preferred. Product separation and isolation is the same as described previously for the chiral acids.

The esters and acids may each also be prepared as described above using the purified enzyme instead of the crude enzyme. This purified enzyme offers more consistent results and easier isolation of products.

For the resolution of esters wherein X is NHNHY, and Y is H or COCH$_2$Ph, a solution or suspension of degassed water or sodium phosphate buffer containing from about 0.001 moles to about 2.0 moles of substrate per litre of reaction volume is adjusted to pH 7.5. A quantity of crude *Candida lipolytica* ester hydrolase corresponding to 20 mg of protein per gram of substrate is added to initiate the reaction. The reaction mixture is placed under a nitrogen atmosphere and stirred at 36 °C. The pH is maintained at 7.3–7.8 by continuous addition of sodium hydroxide until 50% hydrolysis is achieved. The unreacted ester is removed by extraction with methylene chloride, then concentrated in vacuo to afford the (R)-ester in greater than 98% enantiomeric excess. The S aqueous phase is concentrated in vacuo to one tenth its original volume, diluted with three volumes of ethanol, adjusted to pH 6.5 with diethylamine, then aged at 0 °C. to 5 °C. for several hours to precipitate the (S)-acid. To measure the enantiomeric excess and confirm the absolute stereochemistry of the (R)-esters and (S)-acids, the compounds are converted, by acid hydrolysis, to the (R)- and (S)-3-(3,4-dihydroxyphenyl)-2-hydrazino-2-methylpropanoic acids, respectively. The hydrazino acids are then converted to their respective β-N-(1S)-camphanoyl derivatives and compared to similarly derivatized authentic reference standards by HPLC.

For the resolution of esters wherein X represents NH$_2$, the methods described above can also be advantageously applied. The amino esters prepared in this manner are derivatized with 2,3,4,6-tetra-0-acetyl-β-D-glucopyranosyl isothiocyanate instead of (1S)-(−)-camphanoyl chloride, and the diastereomeric excess of the resulting thiourea is determined by HPLC. Alternatively, the optically active esters can be converted to their corresponding acids by acid hydrolysis. These amino acids can be directly analyzed on a protein-based HPLC column to determine the enantiomeric excess.

The following examples further illustrate, but are not intended to limit, the various embodiments of this invention as more fully set forth in the appended claims.

EXAMPLE 1

Preparation of Butyl (±)-2-Hydrazino-2-methyl-3-(4-hydroxy-3-methoxyphenyl)propionate.

To 100 mL of n-butanol saturated with hydrogen chloride gas at 0 °C. to 5 °C. was added 1.98 g (8.2 mmol) of 2-hydrazino-2-methyl-3-(4-hydroxy-3-methoxyphenyl)propionic acid, and the resulting suspension was heated at reflux for 2 h. The reaction mixture was then concentrated to dryness in vacuo. The residue was dissolved in sufficient saturated sodium bicarbonate solution to give a solution of pH 7.5–8.0. The product was extracted with chloroform, dried over magnesium sulfate and then concentrated in vacuo to afford 2.1 g (6.95 mmol, 84% yield) of the hydrazino acid ester. Recrystallization from a mixture of methylene chloride and hexane afforded 1.96 g (80% yield) of the product ester: mp 84.5 °C. to 87.0 °C.; HPLC analysis (C-18 column, 280 nm, $t_R$=16.2 min) showed a single peak; IR (CHCl$_3$ solution) 3540, 2860, 1720, 1515 cm$^{-1}$; $^1$H NMR (400 MHz, CDCl$_3$) δ6.79 (d, 7.6 Hz, 1H), 6.62 (s, 1H), 6.59 (d, 7.6 Hz, 1H), 4.08 (m, 2H), 3.82 (s, 3H), 2.99 (d, 14 Hz, 1H), 2.74 (d, 14 Hz, 1H), 1.58 (m, 2H), 1.34 (m and s, 5H), 0.90 (t, 7.2 Hz, 3H).

EXAMPLE 2

Preparation of Ethyl (±)-2-Hydrazino-2-methyl-3-(4-hydroxy-3-methoxyphenyl)propionate.

The procedure of Example 1 was repeated with ethanol instead of n-butanol. The ethyl 2-hydrazino-2-methyl-3-(4-hydroxy- 3-methoxyphenyl)propionate was obtained in 79% yield after recrystallization from acetonitrile: mp 114 ° C. to 116 ° C.; HPLC analysis (C-18 column, 280 nm, $t_R$=5.3 min) showed a single peak; IR (CHCl$_3$ solution) 3540, 2990, 2940, 1710, 1510 cm$^{-1}$; $^1$H NMR (400 MHz, CDCl$_3$) δ6.79 (d, 7.6 Hz, 1H), 6.63 (s, 1H), 6.60 (d, 7.6 Hz, ! H), 4.14 (q, 7.1 Hz, 2H), 3.83 (s, 3H), 2.99 (d, 13.5 Hz, 1H), 2.74 (d, 13.5 Hz, 1H), 1.34 (s, 3H), 1.24 (t, 7.1 Hz, 3H).

EXAMPLE 3

Preparation of Butyl (±)-2-Amino-2-methyl-3- 3,4-dihydroxyphenyl)propionate.

The procedure of Example 1 was repeated employing 2-amino- 2-methyl-3-(3,4-dihydroxyphenyl)propionic acid rather than 2-hydrazino- 2 -methyl-3-(4-hydroxy-3-methoxyphenyl)propionic acid. The butyl (±)-2-amino-2-methyl-3-(3,4-dihydroxyphenyl)propionate was obtained in a yield of 82%. The product was recrystallized from acetonitrile (77% yield) to give pure ester: mp 121.5 ° C. to 122.0° C.; HPLC analysis (C-18 column, 280 nm, $t_R$=14.5 min) showed >99% purity.

EXAMPLE 4

Preparation of Ethyl (±) -2- (β-N-Phenylacetylhydrazino)-2- methyl- 3-(4-hydroxy-3-methoxyphenyl)propionate.

To a solution of ethyl 2-hydrazino-2-methyl-3-(4-hydroxy- 3-methoxyphenyl)propionate (1.00 g, 3.73 mmol) in 9.2 ml of tetrahydrofuran and 9.2 ml of 1,4-dioxane at 0 ° C. to 5 ° C. was added triethylamine (377.4 mg, 3.73 mmol) followed by dropwise addition of phenylacetyl chloride (576.7 mg, 3.73 mmol). The resulting suspension was stirred at room temperature for 2 h and then concentrated to dryness in vacuo. Purification of this concentrated product by silica gel chromatography (55% hexane in ethyl acetate) yielded 1.01 g (2.62 mmol, 70%) of the ethyl (±)-2-(β-N-phenylacetylhydrazino)- 2-methyl-3-(4-hydroxy-3-methoxyphenyl)propionate: HPLC analysis (C-18 column, 280 nm, $t_R$=17.6 min); IR (CCl$_4$ solution 3050, 3300 (br), 2980, 1720, 1670, 1510 cm$^{-1}$.

EXAMPLE 5

Preparation of Ethyl (R)-2-(β-N-Phenylacetylhydrazino-2-methyl- 3-(4-hydroxy-3-methoxyphenyl)propionate and (S)-2-(β-N-Phenylacetylhydrazino)- 2-methyl-3-(4-hydroxy-3-methoxy)propionic Acid with Crude *Candida lipolytica* Ester Hydrolase A solution of ethyl (+)-2-(α-N-phenylacetylhydrazino)-2-methyl- 3-(4-hydroxy-3-methoxyphenyl)propionate (128.0 mg, 0.331 mmol) in 3.40 ml of ethanol was suspended in 43.0 ml of 50 mM sodium phosphate buffer (pH 7.5). Crude enzyme from *Candida lipolytica* (26 mg of protein) was added, and the resulting suspension was agitated at room temperature for 41 h, at which time 50% hydrolysis was observed. The reaction mixture was extracted with 3×50 ml of methylene chloride. The combined extracts were washed with water, dried over magnesium sulfate, then concentrated in vacuo to yield 55.3 mg (0. 143 mmol) of ethyl (R) -2-(β-N-phenylacetylhydrazino)-2-methyl- 3-(4-hydroxy-3-methoxyphenyl)propionate (43.2 %). The chemical purity by HPLC assay was >97% (C-18 column, 280 nm, $t_R$=17.6 min), with no hydrazino acid present. To determine the enantiomeric purity of the unreacted ester, 5.4 mg of the (R)-ester was heated in a sealed tube with 3 mL of concentrated HCl at 120 ° C. for 2 h to give (R)-2-hydrazino-2-methyl-3-(3,4-dihydroxyphenyl)propionic acid. The resulting acid solution was concentrated to dryness in vacuo. The residue was then derivatized with (1S)-(–)-camphanic chloride using a modification of the method reported by Trimble and Vederas (L. A. Trimble and J. C. Vederas, *J. Am. Chem. Soc.* 108, 6397 (1986)). The diastereomeric excess was found to be >99% by HPLC (C- 18 column, 280 nm, (S,S -diastereomer $t_R$=9.2 min, (R,S)-diastereomer $t_R$=11.7 min) and the (R,S)-stereochemistry of the hydrazide derivative was assigned by comparison to an identically derivatized sample of USP Reference Standard of (S)-2-hydrazino-2-methyl-3-(3,4-dihydroxyphenyl)propioinic acid.

The recovered aqueous layers containing the (S)-2-(β-N-phenylacetylhydrazino)- 2-methyl-3-(4-hydroxy-3-methoxyphenyl) propionic acid were adjusted to pH 3 with 1N HCl and then extracted with 3×50 ml of methylene chloride. The combined extracts were dried over magnesium sulfate, followed by concentration in vacuo to afford the product. Purification by preparative HPLC afforded 6.4 mg (17.9 mmol) of (S)-2-(β-N-phenylacetylhydrazino)-2-methyl-3-(3-methoxy- 4-hydroxyphenyl)propionic acid (11% yield). The (S)-2-(β-N-phenylacetylhydrazino)- 2-methyl-3-(4-hydroxy-3-hydroxyphenyl)propionic acid was hydrolysed to (S)-2-hydrazino-2-methyl-3-(3,4-dihydroxyphenyl)propionic acid and, then derivatized with (1S)-(–)-camphanic chloride as described above. The derivative was analysed by HPLC (C-18 column) and found to have (S,S)-stereochemistry with the diastereomeric excess >99%.

EXAMPLE 6

Preparation of (S)-2-Hydrazino-2-methyl-3-(4-hydroxy-3-methoxyphenyl)propionic Acid with Crude *Candida lipolytica* Ester Hydrolase To a solution of 1.2 g (4.1 retool) of butyl (±)-2-hydrazine- 2-methyl-3-(4-hydroxy-3-methoxyphenyl)propionate in 1 L of sodium phosphate buffer (50 mM, pH 7.5) was added crude *Candida lipolytica* enzyme (12 mg of protein), and the resulting mixture was incubated in a heated orbit shaker (200 rpm) at 36 ° C. The reaction was terminated at 20.5% conversion after 17 h. The unreacted, optically enriched butyl (R)-2-hydrazino-2-methyl-3-(4-hydroxy-3-methoxyphenyl)propionate was removed via extraction with methylene chloride. Lyophilization of the remaining aqueous layer and purification of the resulting solid by preparative reverse phase HPLC afforded the (S)-2-hydrazino-2-methyl-3-(4-hydroxy- 3-methoxyphenyl)propionic acid in 7% yield. A portion of this product (5 mg) was dissolved in 5 mL of sodium phosphate buffer (0.5 M, pH 7.5) and to the resulting solution was added (1S)-(–)-camphanic chloride (50 mg in 1 mL of THF) to give the diastereomeric camphanic hydrazide. HPLC analysis of the hydrazide showed the (S,S)-diastereomer to be in >99% diastereomeric excess (C-18 column, 280 nm, (S,S)-diastereomer $t_R$=21.6 min, (R,S)-diastereomer $t_R$=26.4 min).

EXAMPLE 7

Preparation of (S)-2-Hydrazino-2-methyl-3-(4-hydroxy-3-methoxyphenyl)propionic Acid and Butyl (R)-2-hydrazino-2-methyl- 3-(4-hydroxy-3-methoxyphenyl)propionate with Purified *Candida lipolytica* Ester Hydrolase.

The procedure of Example 6 was repeated with 10.5 mg of the racemic butyl ester and 9.4 mg of purified *Candida lipolytica* ester hydrolase in 2 mL of water. The resulting suspension was incubated at 36° C. in an orbit shaker (200 rpm). After 4.5 h, 48% of the ester was hydrolysed, and at 16 h, 50% hydrolysis of the ester was observed. The unreacted ester was extracted with methylene chloride and purified by preparative HPLC. The remaining aqueous layer was lyophilized and the residue purified by preparative HPLC. Analysis of the enantiomeric excess of the (R)-ester and (S)-acid via their diastereomeric (1S)-(–)-camphanic hydrazide derivatives, prepared as described in Example 5, showed both were greater than 99%.

EXAMPLE 8

Preparation of Ethyl (R)-2-Hydrazino-2-methyl-3-(4-hydroxy- 3-methoxyphenyl)propionate and (S)-2-Hydrazino-2-methyl-3-( 4-hydroxy-3-methoxyphenyl)propanoic Acid with Crude *Candida lipolytica* Ester Hydrolase The procedure of Example 6 was repeated employing ethyl (±)-2-hydrazino-2-methyl-3-(4-hydroxy-3-methoxyphenyl)propionate rather than butyl (±)-2-hydrazino-2-methyl-3-(4-hydroxy- 3-methoxyphenyl)propionate. The enzymatic hydrolysis was allowed to proceed to 50% conversion and the unreacted ethyl ester was extracted with methylene chloride. A portion of the ester was hydrolysed in concentrated HCl, and then derivatized with (1S)-(–)-camphanic chloride as described in Example 5. The camphanic hydrazide derivative was found to be the (R,S)-diastereomer, and the diastereomeric excess was >98%.

EXAMPLE 9

Preparation of (S)-2-Hydrazino-2-methyl-3-(4-hydroxy-3-methoxyphenyl)propionic Acid Using Serine Carboxypeptidase Y.

The procedure of Example 6 was repeated using ethyl (±)-2-hydrazino- 2-methyl-3-(4-hydroxy-3-methoxyphenyl-)propionate (14 mg) and serine carboxypeptidase Y from Boehringer Mannheim (1 mg of protein). After incubation at pH 7.4 for 20 h at 22° C., the conversion was 46%. The reaction mixture was then extracted with methylene chloride to remove the unreacted ester. The aqueous layer, which contained the (S)-3-O-methylcarbidopa, was buffered with sodium dihydrogen phosphate then derivatized with (1S)-(–)-camphanic chloride. HPLC analysis of the hydrazide showed the (S,S)-diastereomer to be present in >98% diastereomeric excess (C-18 column, 280 nm).

EXAMPLE 10

Preparation of (S)-2-Hydrazino-2-methyl-3-(4-hydroxy-3-methoxyphenyl)propionic Acid Using Serine Carboxypeptidase P.

The procedure of Example 9 was repeated using ethyl (±)-2-hydrazino- 2-methyl-3-(4-hydroxy-3-methoxyphenyl-)propionate (8 mg) and carboxypeptidase P from Sigma (1 mg of protein). After incubation at pH 7.4 for 42 h at 22° C., the conversion was 33%. The diastereomeric excess of the camphanic hydrazide derivative of (S)-3-O-methylcarbidopa was >96%.

This procedure was repeated at pH 5.5. After 20 h the conversion was 50%, and the diastereomeric excess of the camphanic hydrazide derivative of (S)-3-O-methylcarbidopa was >98%.

EXAMPLE 11

Resolution of Ethyl (±)-2-Hydroxy-2-methyl-3-(4-hydroxy- 3-methoxyphenyl)propionate with Crude *Candida lipolytica* Ester Hydrolase To a suspension of 109 mg (0.43 mmol) of ethyl (±)-2-hydroxy- 2-methyl-3-(4-hydroxy-3-methoxyphenyl)propionate in 4.6 mL of sodium phosphate buffer (50 mM, pH 7.5) is added crude enzyme from *Candida lipolytica* (7 mg of protein), and the reaction mixture is stirred at 20° C. After 2.5 h, 50% conversion is observed by HPLC (C-18 column, 280 nm, acid $t_R$=7 min, ester $t_R$=10.2 min). The reaction mixture is diluted with 20 mL of $H_2O$ and the unreacted ester is extracted with ethyl acetate (2×25 mL). The combined extracts are washed with saturated sodium bicarbonate solution, dried ($MgSO_4$) and concentrated in vacuo to afford 27 mg of unreacted ester (HPLC shows one peak). The enantiomeric excess of the unreacted ester is determined by HPLC analysis (Chiracel OD column from J. T. Baker, 280 nm, first enantiomer $t_R$=7 min, second enantiomer $t_R$=10.3 min) to be >99% for the faster eluting enantiomer.

EXAMPLE 12

Resolution of Ethyl (±)-2-Hydroxy-2-methyl-3-( 3,4-dimethoxy-phenyl)propionate with Crude *Candida lipolytica* Ester Hydrolase.

To a suspension of ethyl (±)-2-hydroxy-2-methyl-3-( 3,4-dimethoxyphenyl)propionate (333.0 mg, 1.24 mmol) in 50 mL of 50 mM sodium phosphate buffer pH 7.5 is added crude *Candida lipolytica* ester hydrolase (22.6 mg of protein). After 24 h, 62% conversion is observed by HPLC (C18 column, 254 nm detection, acid $t_R$=5.8 min and ester $t_R$=11.6 min). The reaction is treated with a Celite filtration and then extracted with 2×25 mL ethyl acetate. The combined extracts are treated with brine, dried with magnesium sulfate, then concentrated in vacuo to yield ethyl (R)-2-hydroxy-2-methyl- 3-(3,4-dimethoxyphenyl)propionate (127.4 mg, 0.475 mmol, 38.3%). The enantiomeric excess of the unreacted ester is determined by HPLC analysis (Chiracel OD column from J. T. Baker, 280 nm, (S)-enantiomer $t_R$=6.6 min and (R)-enantiomer $t_R$=8.3 min) to be 99% (R)-enantiomer.

EXAMPLE 13

Resolution of Ethyl (±)-2-Hydroxy-2-methyl-3-(3,4-dimethoxyphenyl)propionate with Serine Carboxypeptidase Y.

To a suspension of ethyl (±)-2-hydroxy-2-methyl-3-( 3,4-dimethoxyphenyl)propionate (301.1 mg, 1.12 mmol) in 50 mL of 50 mM sodium phosphate buffer pH 7.5 is added carboxypeptidase Y from Bakers Yeast (7.6 mg of protein). After 23 h, 90.6% conversion is observed by HPLC ($C_{18}$ column, 254 nm detection, acid $t_R$=5.8 min and ester $t_R$=11.6 min). The reaction is extracted with 2×25 mL ethyl acetate. The combined extracts are treated with brine, dried with magnesium sulfate, then concentrated in vacuo to yield ethyl (R)- 2-hydroxy-2-methyl-3-(3,4-dimethoxyphenyl)propionate (36.2 mg, 0.135 mmol, 12.1%). The enantiomeric excess of the unreacted ester is determined by HPLC analysis (Chiracel OD column from J. T. Baker, 280 nm, (S)-enantiomer $t_R$=6.6 min and (R)-enantiomer $t_R$=8.3 min) to be 31.2% (R -enantiomer.

EXAMPLE 14

Resolution of Ethyl (±)-2-Hydroxy-2-methyl-3-( 3,4-dimethoxyphenyl)-propionate with Serine Carboxypepmidase W.

To a suspension of ethyl (±)-2-hydroxy-2-methyl-3-(3,4-dimethoxlphenyl)propioname (51.4 mg, 0.192 mmol) in 10 mL of 50 mM sodium phosphate buffer pH 7.5 is added carboxypeptidase W (5.7 mg of solid). After ca. 8 h of stirring at ambient temperature, 56% conversion is observed by HPLC ($C_{18}$ column, 254 nm detection, acid $t_R$=5.6 min and ester $t_R$=11.0 min). The reaction is diluted with 10 mL saturated bicarbonate followed by extraction with 2×10 mL ethyl acetate. The combined extracts are treated with brine, dried with magnesium sulfate, then concentrated in vacuo to yield ethyl (R)- 2-hydroxy-2-methyl-3-(3,4-dimethoxyphenyl)propionate (15.5 mg, 57.8 mmol, 30.2%). The enantiomeric excess of the unreacted ester is determined by HPLC analysis (Chiracel OD column from J. T. Baker, 254 nm, (S)-enantiomer $t_R$=6.6 min and (R)-enantiomer $t_R$=8.3 min) to be 99% (R)-enantiomer.

EXAMPLE 15

Resolution of (±)-α-Methyltryptophan Methyl Ester with Serine Carboxypeptidase Y.

To a suspension of (±)-α-methyltryptophan methyl ester (150.0 mg, 0.646 mmol) in 50 mL of 50 mM sodium phosphate buffer pH 7.5 was added carboxypeptidase Y from Bakers Yeast (6.4 mg). The resulting suspension was stirred at ambient temperature. After 4 h, 75% conversion was observed by HPLC ($C_{18}$ column, 254 nm detection, acid $t_R$=9.0 min and ester $t_R$=11.9 min). The reaction was extracted with 2×25 mL chloroform. The combined extracts were treated with brine, dried with magnesium sulfate, then concentrated in vacuo to yield (R)-α-methyltryptophan methyl ester (15.6 mg, 67.2 mmol, 10.4%). A portion of this α-methyl amino ester was derivatized with 2,3,4,6-tetra-O-acetyl-β-D-glucopyranosyl isothiocyanate (TAGIT). HPLC analysis of the resulting thioureas showed the (R,S)-diastereomer to be in >99% diastereomeric excess ($C_{18}$ column, 254 nm detection, S,S)-diastereomer $t_R$=15.9 min and (R,S)-diastereomer $t_R$=16.8 min).

EXAMPLE 16

Resolution of (±)-α-Methyltryptophan Methyl Ester with Serine Carboxypeptidase W.

To a suspension of (±)-α-methyltryptophan methyl ester (79.5 mg, 0.342 mmol) in 30 mL of 50 mM sodium phosphate buffer pH 7.5 was added carboxypeptidase W (3.0 mg of solid). The resulting suspension was stirred at ambient temperature. After 6.5 h, 56% conversion was observed by HPLC ($C_{18}$ column, 280 nm detection, amino acid $t_R$=8.2 min and amino ester $t_R$=11.1 min). The reaction was adjusted to pH 12 by the addition of 2 N KOH and then extracted with 1×15 and 1×20 mL ethyl acetate. The combined extracts were treated with brine, dried with magnesium sulfate, then concentrated in vacuo to yield (R)-α-methyltryptophan methyl ester (10.4 mg, 44.8 mmol, 13.1%). The enantiomeric excess of the unreacted amino ester was determined by chiral HPLC (Uttron ES-OVM column from Shinwa Chemical Industries, Ltd., 280 nm, (R)-enantiomer $t_R$=13.7 min and (S)-enantiomer $t_R$=18.8 min) to be 89.9% (r)-enantiomer.

EXAMPLE 17

Resolution of (±)-α-Methyltryptophan Methyl Ester with Serine Carboxypeptidase P.

To a suspension of (±)-α-methyltryptophan methyl ester (102.8 mg, 0.443 mmol) in 25 mL of 50 mM sodium phosphate buffer pH 6.0 was added carboxypeptidase P from *Penicillium janthinellum* (3.2 rag of protein). The resulting suspension was stirred at ambient temperature. After 2 h, 50% conversion was observed by HPLC ($C_{18}$ column, 254 nm detection, acid $t_R$=9.0 min and ester $t_R$=11.9 min). The reaction was adjusted to pH 10 by the addition of 2N KOH and then was extracted with 3×25 mL ethyl acetate. The combined extracts were treated with brine, dried with magnesium sulfate, then concentrated in vacuo to yield (R)-α-methyltryptophan methyl ester (40 mg, 172 mmol, 38.8%): $^1$H NMR (400 MHz, $CDCl_3$-THS) δ8.34 (bs, 1H), 7.61 (d, 7.9 Hz, 1H), 7.30 (d, 8.54 Hz, 1H), 7.16 (dd, 7.0, 7.0 Hz, 1H), 7.10 (dd, 7.6, 7.6 Hz, 1H), 6.98 {s, 1H), 3.64 (s, 3H), 3.29 (A of AB, JAB=14.6 Hz, 1H), 3.01 (B of AB, JAB=14.6 Hz, 1H), 1.92 (bs, 2H), 1.45 (s, 3H); $^{13}$C NMR (100 MHz, $CDCl_3$) δ177.85, 135.99, 128.08, 123.30, 121.91, 119.44, 119.09, 111. 07, 110.65, 59.14, 52.09, 36.38, 26.61. A portion of this (R)-α-methyl amino ester (1.6 mg, 6.89 mmol) was refluxed in 20 mL 6N HCl for 2 h then concentrated in vacuo to afford (R)-α-methyltryptophan hydrochloride (1.6 mg, 6.28 mmol, 91.1%). The enantiomeric excess of the amino acid was determined by HPLC analysis ((D)-Penicillinamine column from Phenomonex, detection 254 nm, (R)-enantiomer $t_R$=12.4 min and (S)-enantiomer $t_R$=14.6 min) to be >99% (R)-enantiomer.

EXAMPLE 18

Resolution of Ethyl (±)-N-Acetyl-α-methylleucinate with Serine Carboxypeptidase Y.

To a solution of ethyl N-acetyl-(±)-α-methylleucinate (250.0 mg, 1.16 mmol) in 70 mL of 50 mM sodium phosphate buffer pH 7.5 is added carboxypeptidase Y from Bakers Yeast (10.4 mg of protein). After 120 h, 50% conversion is observed by HPLC ($C_{18}$ column, 210 nm detection, amido acid $t_R$=8.1 rain and amido ester $t_R$=10.7 min). The reaction is extracted with 3×25 mL chloroform. The combined extracts are dried with magnesium sulfate and concentrated in vacuo to yield ethyl (R)-N-acetyl-α-methylleucinate (120 mg, 0.557 mmol, 48%). A portion of this (R)-α-methyl amido ester (70 mg, 0.325 mmol) is refluxed in 50 mL 6N HCl for 2 h then concentrated in vacuo to afford (R)-α-methylleucine hydrochloride (70 mg). The enantiomeric excess of the amino acid is determined by HPLC analysis ((D)-Penicillinamine column from Phenomonex, detection 254 nm, (S)-enantiomer $t_R$=4.6 min and (R)-enantiomer $t_R$=7.4 min) to be >98% (R)-enantiomer.

The recovered aqueous layer containing the (S)-N-acetyl-α-methylleucine is adjusted to pH 2 by the addition of 1M phosphoric acid and is extracted with 3×25 mL ethyl acetate. The combined extracts are dried over magnesium sulfate and concentrated in vacuo to yield (S)-N-acetyl-α-methylleucine (100 mg, 0.534 mmol, 46.0%). A portion of this (S)-N-acetyl-α-methyl amido acid (100 mg, 0.534 mmol) is refluxed in 50 mL 6N HCl for 2 h then concentrated in vacuo to afford (S)-α-methylleucine hydrochloride (90 mg, 0.495 mmol, 92.7%). The enantiomeric excess of the amino acid is determined by HPLC analysis ((D)-Penicillinamine column from Phenomonex, detection 254 nm, (S)-enantiomer $t_R$=4.6 min and (R)-enantiomer $t_R$=7.4 min) to be >99% (S)-enantiomer.

EXAMPLE 19

Resolution of Methyl (±)-α-Difluoromethylphenylalanate with Crude Candida lipolytice Ester Hydrolase.

To a suspension of methyl (±)-α-difluoromethylphenylalanate (0.50 g, 2.18 mmol) in 100 mL 50 mM sodium phosphate buffer pH 7.5 is added crude Candida limolytica ester hydrolase (100 mg of total protein). The resulting suspension is stirred at 35° C. and maintained at pH 7.3 by dropwise addition of 2N KOH as necessary for ca. 120 h at which time ca. 68% enzymatic hydrolysis is observed by HPLC ($C_{18}$ column, 254 nm detection, amino acid $t_R$=5.8 min and amino ester $t_R$= 13.6 min). To the reaction is added Celite (21 g), 100 mL deionized water, and 100 mL chloroform. The resulting suspension is filtered and the layers of the filtrate are separated. The aqueous layer is re-extracted with 1×100 mL chloroform. The combined extracts are treated to a brine wash, dried over magnesium sulfate, and then concentrated in vacuo to afford methyl (S)-α-difluoromethylphenylalanate (52.1 mg, 0.227 mmol, 10.4%). The enantiomeric excess of the unreacted amino ester is determined by HPLC analysis (Chiracel OD column from J. T. Baker, 254 nm, (S)-enantiomer $t_R$=8.3 min and (R)-enantiomer $t_R$=9.4 min) to be ca, 97% (S)-enantiomer.

EXAMPLE 20

Resolution of Methyl (±)-α-Difluoromethylphenylalanate with Purified *Candida lipolytica* Ester Hydrolase.

To a suspension of methyl (±)-α-difluoromethylphenylalanate (0.22 g, 0.960 mmol) in 100 mL of 50 mM sodium phosphate buffer pH 7.5 is added purified *Candida lipolytica* ester hydrolase (5.7 mg of protein). After 120 h at 37° C., 52.6% conversion is observed by HPLC ($C_{18}$ column, 254 nm detection, amino acid $t_R$=6.2 min and amino ester $t_R$=14.0 min). The reaction is extracted with 2×50 mL of chloroform. The combined extracts are dried over magnesium sulfate then concentrated in vacuo to yield methyl (S)-α-difluoromethylphenylalaname (84.1 mg, 0.367 mmol, 38.2%). The enantiomeric excess of the unreacted amino ester is determined by HPLC analysis (Chiracel OD column from J. T. Baker, 254 rim, (S)-enantiomer $t_R$=8.4 min and (R)-enantiomer $t_R$=9.5 min) to be 94.1% (S)-enantiomer.

EXAMPLE 21

Resolution of Methyl (±)-α-Difluoromethylphenylalanate with Carboxypeptidase Y.

To a suspension of methyl (±)-α-difluoromethylphenylalanate (145.9 mg, 0.637 mmol) in 50 mL of 50 mM sodium phosphate buffer pH 7.5 is added carboxypeptidase Y from Bakers Yeast (6.9 mg of protein). After 192 h at ambient temperature, 54.2% conversion is observed by HPLC ($C_{18}$ column, 254 nm detection, amino acid $t_R$=6.2 min and amino ester $t_R$=14.0 min). The reaction is extracted with 3×25 mL of chloroform. The combined extracts are dried over magnesium sulfate then concentrated in vacuo to yield methyl (S)-α-difluoromethylphenylalanate (10 mg, 43.6 mmol, 6.9%). The enantiomeric excess of the unreacted amino ester is determined by HPLC analysis (Chiracel OD column from J. T. Baker, 254 nm, (S)-enantiomer $t_R$=13.3 min and (R)-enantiomer $t_R$=16.8 min) to be ca. 13% (S)-enantiomer.

EXAMPLE 22

Spectrophotometric Assay of Serine Carboxypeptidase and *Candida lipolytica* Ester Hydrolase Activities.

The target ester-hydrolyzing activity was evaluated spectrophotometrically in both crude and purified enzyme preparations using thiopropyl D,L-N-acetyl-α-methylphenylalanate as the substrate. The rate of thioester hydrolysis was monitored by coupling the release of propanethiol to a non-enzymic thio-disulfide interchange reaction with dithionitrobenzoate. The production of the resulting thionitrobenzoate anion was monitored at 410 nm. The standard assay mixture contained 50 mM Napes buffer pH 7.5, 1.0 mM EDTA, 2.0 mM thiopropyl D-L-N-acetyl-α-methylphenylalanate, 1.0 mM DTNB and 10% DHF. One unit of activity is defined as the amount of enzyme required to release 1 mmol of propanethiol per minute at 25° C.

EXAMPLE 23

Isolation of a Crude Protein Fraction Containing Ester Hydrolase Activity from *Candida lipolytica* Fermentation Broth.

Fermentations of *Candida lipolytica* strain NRRL Y-1094 (United States Department of Agriculture, Peoria, Ill.) were carried out at pH 6.0–7.0 at 30° C. in medium containing the following constituents: 0.3% yeast extract, 0.3% malt extract, 0.5% Bacto peptone, 0.14% potassium dihydrogen phosphate, 0.035% disodium hydrogen phosphate and 1% glucose. Enzyme activity was apparent once the culture attained stationary phase with an OD590 of approximately 60. A yield of approximately 0.6 mg of ester hydrolase per liter of culture was obtained under these conditions with maximum expression typically found after 4–5 days of fermentation. Upon termination of fermentation, the cells were removed by centrifugation at 4000×g for 30 min and the fermentation broth was adjusted to 1.8 H ammonium sulfate. The cell supernatant from a 14 L fermentation was then pumped onto a 0.5 L phenyl sepharose column that had been equilibrated in 50 mM Hepes buffer, pH 7.5, containing 1.0 mM EDTA and 1.8 M ammonium sulfate. After the culture broth had been applied to the resin, the column was washed with 2 volumes of equilibration buffer and the protein fraction containing the target ester hydrolase eluted with 1.2 L of 50 mM Hepes buffer, pH 7.5 containing 1.0 mM EDTA. The enzyme fraction was then further concentrated and desalted by adjusting the solution to 30% polyethylene glycol (Av. MW=8000). The precipitated proteins were then isolated by centrifugation at 7000× g for 30 min and the resulting pellet was dissolved in approximately 70 mL of 10 mM phosphate buffer, pH 6.5, containing 1.0 mM EDTA. This concentrated, partially purified ester hydrolase-containing fraction may be subjected to column chromatography as described in Example 24.

EXAMPLE 24

Purification of Ester Hydrolase from Crude *Candida lipolytica* Lipase Preparations.

The purification buffer utilized for all steps was 10 mM sodium phosphate, pH 6.5, containing 1.0 mM EDTA. Ten (10) g crude *Candida lipolytica* lipase (Fluka) was suspended in 100 mL buffer and mixed gently for approximately 20 min. Insoluble components were removed from the protein solution by centrifugation at 1,600×g for 5 min. Solid polyethylene glycol was then added to the clarified supernatant to a final concentration of 30% (w/v) and the solution allowed to mix gently for 30 min at 22° C. The precipitated proteins were then collected by centrifugation at 18,000×g for 30 min and the resulting protein pellet was dissolved in 20 mL buffer. The resulting viscous solution was dialyzed against purification buffer to remove residual polyethylene glycol.

The crude dialyzed protein fraction was applied to a 100 mL Blue B Matrex™ dye column (Amicon, Danvers, Mass.) that had been equilibrated in purification buffer. The protein solution was allowed to adsorb to the resin for approximately 30 min and the resin was then washed with approximately 400 mL purification buffer until the absorbance at 280 nm was less than 0.05 absorbance units. The desired ester hydrolase was eluted from the column with approximately 150 mL purification buffer that had been adjusted to 1.2 M KCl. Fractions of 5 mL were collected during the elution step and only those fractions containing enzyme activity were pooled. Typically, the enzyme eluted over 6–7 fractions (ca. 30 mL).

Ester hydrolase purified using this protocol had a specific activity of approximately 0.07 units mg$^{-1}$ using the activity assay described in Example 23 and the Bradford assay (Bio-Rad, Bethesda, Md.) for protein evaluation. The activity of the ester hydrolase was verified by the preparation of (S)-2-hydrazino-2-methyl- 3-(4-hydroxy-3-methoxyphenyl-)propionic acid using a small scale version of the method described in Example 6.

EXAMPLE 25

Assay of Peptidase Activity of *Candida lipolytica* Ester Hydrolase.

Peptidase activity was evaluated as described by Hayashi (*Methods in Enzymology*, 1976, vol. 45, p.568) using the protected dipeptide N-CBZ-Phe-Ala as substrate (Johansen et al., Carlsberg Res. Commun., 1976, vol. 41, p. 4). Between 0.01 and 1 mg of *Candida lipolytica* ester hydrolase, dissolved in 50 mM 2-[N-morpholino]ethanesulfonic acid (Mes) buffer at pH 6.75, is added to a solution of the substrate in 50 mM Hes buffer to give a final substrate concentration of 2 mM and a total volume of 3 ml. The reaction is followed spectrophotometrically by measuring the decrease in absorbance at 230 nm at 25° C. Based on a change in molar absorptivity of 191.5 for cleavage of the substrate's peptide bond, a rate of 1.2 units per mg of enzyme was observed. One unit is defined as the amount of enzyme that catalyzes the cleavage of one micromole peptide bonds per minute under the conditions specified above.

EXAMPLE 26

Assay of Amidolytic Activity of *Candida lipolytica* Ester Hydrolase.

The chromogenic carboxypetidase substrate benzoyl-L-tyrosine p-nitroanilide was used as described by Hayashi (*Methods in Enzymology*, 1977, vol. 45, p. 571) to assay *Candida lipolytica* ester hydrolase. A 1.5 mM solution of benzoyl-L-tyrosine p-nitroanilide prepared in dimethylformamide and an enzyme solution in 0.1M sodium phosphate buffer, pH 7.0 are added to a spectrophotometer cuvette with 0.1 M sodium phosphate buffer, pH 7.0, in a ratio that results in 0.15 mM benzoyl-L-tyrosine p-nitroanilide, 0.09 molar sodium phosphate, and enzyme concentration of 0.01 to 0.1 units per mL. The increase in absorption at 410 nm is followed at 25 ° C. Based on a molar extinction coefficient of 8800 for p-nitroaniline, a reaction rate corresponding to 0.2 units per mg enzyme is observed. One unit is defined as the amount of enzyme required to cleave one micromole of anilide bonds per minute under the conditions specified above.

EXAMPLE 27

Inactivation of *Candida lipolytica* Ester Hydrolase by Diisopropyl Fluorophosphate.

To solutions of between 0.1 and 1 mg/mL *Candida lipolytica* ester hydrotase in 10 mM sodium phosphate buffer, pH 6.5, solutions of diisopropyl fluorophosphate (DFP) in isopropanol are added such that final concentrations of 10% (v/v) isopropanol and between 0 and 1 mM DFP are achieved. All solutions are kept at room temperature. Five minutes after addition of the DFP solution each mixture is assayed as described in Example 22. The relative activities of the hydrolase are approximately 0% at 1 mM DFP, 40% at 0.1 mM DFP, 60% at 0.01 mM DFP, 90% at 0.001 mM DFP and 100% in the absence of DFP.

---

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 20 Amino Acids
( B ) TYPE: Amino Acid Sequence
( C ) TOPOLOGY: Linear ( i i ) MOLECULE TYPE: Protein ( x i ) SEQUENCE DESCRIPTION: SEQ ID NO:1:

```
SER VAL PRO GLY ASP LEU GLY LEU ASP ASP
 1               5                    10

VAL GLN GLN TYR THR GLY TYR LEU THR ALA
                    15                   20
```

---

What is claimed is:

1. A method of separating the enantiomers of racemic carboxylic acid esters of general formula

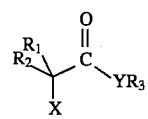

wherein $R_1$ represents alkyl, substituted alkyl, arylalkyl or substituted arylalkyl; $R_2$ represents alkyl, haloalkyl or substituted alkyl; $R_3$ represents an alkyl moiety having from 1 to 8 carbon atoms, substituted alkyl, alkenyl, substituted alkenyl, alkynyl, substituted alkynyl, aryl, substituted aryl, arylalkyl or substituted arylalkyl; and X represents amino, alkylamino, arylalkylamino, arylamino, acylamino, hydrazino, alkylhydrazino, arylalkylhydrazino, arylhydrazino, acylhydrazino, hydroxyl, or alkoxy; and Y represents oxygen or sulfur; provided that $R_1$ and $R_2$ and X are different from each other, by the preferential enzymatic hydrolysis of the (S)-enantiomer of the ester, said method comprising contacting the racemic ester in an aqueous medium with a serine carboxypeptidase selected from the group consisting of serine carboxypeptidase % serine carboxypeptidase P and serine carboxypeptidase W to hydrolyze from about 5% to about 95% of the ester, and separating the hydrolysis product from the unreacted starting material.

2. The method of claim 1 wherein the aqueous solution contains a buffer.

3. The method of claim 1 wherein the aqueous solution contains up to about 75% of an organic solvent.

4. The method of claim 3 wherein the organic solvent is selected from the group consisting of methanol, ethanol, 1-propanol, 2-propanol, acetonitrile, acetone, 2-butanone, dimethylformamide and dimethylsulfoxide.

5. The method of claim 1 wherein the hydrolysis reaction is carried out at a temperature of from about 0° C. to about 55

6. The method of claim 1 wherein X is selected from the group consisting of hydroxyl, amino, acylamino, hydrazino and acylhydrazino.

7. The method of claim 1 wherein X is halogen or halomethyl.

8. The method of claim 6 wherein X is selected from the group consisting of OH, $NHR_5$, and NHNHRS; $R_5$ represents H, $COCH_3$ or $COCH_2Ph$; $R_3$ is $C_1$ to $C_8$ n-alkyl; R1 is $CH_3$ or $CHF_2$; and $R_2$ is represented by the formula

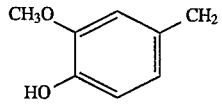

9. The method of claim 8 wherein $R_5$ is H.

10. The method of claim 8 wherein $R_3$ is butyl, ethyl, or methyl.

11. The method of claim 8 wherein X is $NHR_5$.

12. The method of claim 8 wherein the hydrolyzed enantiomer is produced in at least about 13% enantiomeric excess.

* * * * *

UNITED STATES PATENT AND TRADEMARK OFFICE
CERTIFICATE OF CORRECTION

PATENT NO. : 5,492,830
DATED : February 20, 1996
INVENTOR(S) : Helmut Kallwass, Christopher Yee, Todd Blythe, Spencer Shames and Elizabeth Rogers It is certified that error appears in the above-indentified patent and that said Letters Patent is hereby corrected as shown below:

Column 19, line 14, should read --group consisting of serine carboxypeptidase Y, serine car- --.

Signed and Sealed this

Twenty-seventh Day of August, 1996

Attest:

BRUCE LEHMAN

Attesting Officer

Commissioner of Patents and Trademarks